United States Patent
Suzuki et al.

[11] Patent Number: 5,603,961
[45] Date of Patent: Feb. 18, 1997

[54] SUSTAINED RELEASE MULTI-CORE MICROSPHERE PREPARATION AND METHOD FOR PRODUCING THE SAME

[75] Inventors: Takehiko Suzuki, Osaka-fu; Yukiko Nishioka, Toyonaka; Yasuhisa Matsukawa, Osaka; Akihiro Matsumoto, Hirakata; Masao Kobayashi, Kyoto, all of Japan

[73] Assignee: Tanabe Seiyaku Co., Ltd., Osaka, Japan

[21] Appl. No.: 128,692

[22] Filed: Sep. 30, 1993

[30] Foreign Application Priority Data

Oct. 1, 1992 [JP] Japan .................... 4-263460

[51] Int. Cl.⁶ .................... A61K 9/50; A61K 9/14; A61K 9/16; B01J 13/02
[52] U.S. Cl. .................... 424/502; 424/489; 424/490; 424/497; 424/501; 424/402.21; 514/937; 514/938; 264/4.1; 264/4.33; 264/4.6
[58] Field of Search .................... 424/489, 490, 424/497, 501, 451, 502; 514/937, 938; 264/4.1, 4.33, 4.6; 428/402.21

[56] References Cited

U.S. PATENT DOCUMENTS

| | | | |
|---|---|---|---|
| 4,940,588 | 7/1990 | Sparks et al. | 424/497 |
| 5,100,669 | 3/1992 | Hyon et al. | 424/497 |

FOREIGN PATENT DOCUMENTS

| | | |
|---|---|---|
| 0052510A2 | 5/1982 | European Pat. Off. |
| 0145240A2 | 6/1985 | European Pat. Off. |
| 0190833A2 | 8/1986 | European Pat. Off. |
| 0263490A2 | 4/1988 | European Pat. Off. |
| 0330180A1 | 8/1989 | European Pat. Off. |
| WO88/08300 | 11/1988 | WIPO |
| WO89/07935 | 9/1989 | WIPO |

*Primary Examiner*—Carlos Azpuru
*Attorney, Agent, or Firm*—Finnegan, Henderson, Farabow, Garrett & Dunner, L.L.P.

[57] ABSTRACT

Sustained release multi-core microsphere preparation which shows high incorporation efficiency of medicament and can release the medicament at a specific rate, which comprises two or more biodegradable polymers and a pharmaceutically active ingredient, and has the medicament incorporated into microregions which are produced by one of these polymers (the first polymer), and these microregions are distributed in other biodegradable polymers (the second polymer), or a method for producing the same.

14 Claims, 3 Drawing Sheets

STRUCTURE OF MICROSPHERE PREPARATION OF THE INVENTION

SUSTAINED RELEASE MULTI-CORE MICROSPHERE PREPARATION AND METHOD FOR PRODUCING THE SAME

The present invention relates to a sustained release pharmaceutical composition comprising a pharmaceutically active ingredient and biodegradable polymers. More particularly, the present invention relates to a sustained release multi-core microsphere preparation, incorporating a pharmaceutically active ingredient in high efficiency and being able to release it at a controlled rate, which is prepared by using specifically two or more biodegradable polymers, and a method for producing thereof.

RELEVANT ART

Hitherto, there have been known some microspheres using a biodegradable polymer, which can effectively sustain a pharmacological activity of a pharmaceutically active ingredient for a long period of time, and there have also been known various methods for producing thereof. For instance, European Patent Publication No. 52510-A discloses a method for producing a microcapsule-type microsphere preparation prepared by a phase separation technique using coacervation-inducing agents. However, during the process disclosed in said European Patent Publication, aggregation of particles easily happens, and since nonvolatile mineral oil or vegetable oil is used therein as a dispersion solvent, there are some difficulties in separation and washing of the resulting microspheres. Moreover, the resulting microspheres are often hollow, and hence, it is difficult to obtain microspheres having a certain and constant quality.

In order to overcome the above mentioned defects, there are disclosed several methods for producing microspheres by a solvent evaporation method, for example, European Patent Publication No. 145240-A and European Patent Publication No. 190833-A disclose a technique using a water in oil in water (W/O/W) emulsion, European Patent Publication No. 330180-A discloses one with an oil in oil (O/O) emulsion, and European Patent Publication No. 263490-A discloses one with an oil in water (O/W) emulsion.

In general, since most of pharmaceutically active substances, which need a sustained release property, are water-soluble, the preparation of microspheres from O/O emulsion using the solvent evaporation method is advantageous for incorporating a pharmaceutically active ingredient into microspheres. However, it is difficult to remove completely the nonvolatile solvents used in a dispersion phase from microspheres, and there are many other problems, for example, safety of operation, or environmental problems. Besides, there is used a mineral oil or vegetable oil as an external oil phase in W/O emulsion, and hence, it is difficult to collect or to wash the resulting microspheres, and the remaining oil in microspheres is a significant problem.

On the other hand, in the above mentioned W/O/W method or O/W method, the external phase is an aqueous solution, and hence, there is no such problem as the remaining oil in microspheres like as mentioned in O/O method. However, the pharmaceutically active ingredient in oil phase often dissolves out into the external aqueous solution so that the incorporation efficiency of the pharmaceutically active ingredient into microspheres becomes low.

In order to overcome the above mentioned defects, there are disclosed W/O/W methods in European Patent Publication No. 145240-A and European Patent Publication No. 190833-A, which comprises dissolving gelatin into the internal aqueous phase. However, the emulsification process must be repeated twice in W/O/W method, and as a result, the proceedings are complicated so that it is necessary to define strictly the conditions for each step in order to obtain microspheres having a certain and constant properties. In addition, this method cannot be effectively applied to every pharmaceutically active ingredient, and since such additives as gelatin, arginine, gum arabic, etc., are used to sustain the medicament in the internal aqueous phase in this method, it is also important and significant problem to sterilize these additives and further to avoid pyrogenation of these additives. Further, this method is disadvantageous in that the medicament rapidly releases from microspheres within a short period of time (Burst-effect).

Under the above mentioned circumstances, it has been desired to produce microspheres, which can incorporate a pharmaceutically active ingredient at a high rate, in viewpoint of operation efficiency and safety.

BRIEF DESCRIPTION OF THE INVENTION

An object of the present invention is to provide a sustained release multi-core microsphere preparation which comprises a pharmaceutically active ingredient and two or more biodegradable polymers, and has an internal structure consisting of microregions which are produced by one of these biodegradable polymers (the first polymer) and contain the pharmaceutically active ingredient, and a region which is produced by other polymer(s) (the second polymer) and in which these microregions are distributed. Another object of the present invention is to provide a method for producing said sustained release multi-core microsphere preparation.

DETAILED DESCRIPTION OF THE INVENTION

Figure 3:
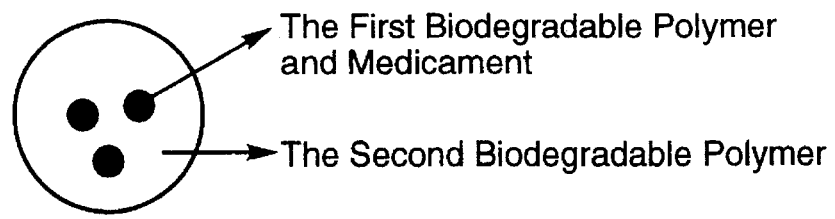
FIG. 3 shows a structure of the present microsphere preparation.

The present inventors have intensively studied in order to overcome the above mentioned defects of the conventional preparations, and have found that an oil in oil (O/O) emulsion has been obtained by dissolving two or more biodegradable polymers individually in the same or different water-immiscible organic solvents, combining these solutions by which these solutions do not mix but separate, followed by stirring vigorously these solutions. Further, the present inventor have found that when a pharmaceutically active ingredient is added to this O/O emulsion, the pharmaceutically active ingredient is incorporated selectively in one of these polymers (oil phases) to give a discontinuous emulsion, which is further dispersed in water to give an oil in oil in water (O/O/W) emulsion. The O/O/W emulsion thus obtained is subjected to the solvent evaporation to give microspheres having the pharmaceutically active ingredient incorporated insularly in multiple. In this case, as shown in FIG. 3, the pharmaceutically active ingredient is mostly incorporated and distributed into the internal polymer phase, and is dispersed in alloy-state in the internal phase, but not in the external polymer phase. The external polymer phase prevents the pharmaceutically active ingredient from contacting with the external aqueous solution, by which the microsphere preparation prepared from O/O/W emulsion having the above mentioned structure shows high incorporation efficiency of the pharmaceutically active ingredient, and does not show the initial burst at the initial stage of the dissolution test, that is, the microsphere preparation of the present invention show the sustained release property.

The microsphere preparation of the present invention is a sustained release multi-core microsphere preparation which comprises a pharmaceutically active ingredient and two or more biodegradable polymers, and has an internal structure consisting of microregions produced by one of these biodegradable polymers containing the pharmaceutically active ingredient, and a region produced by other polymer(s) in which these microregions are distributed.

The pharmaceutically active ingredient used in the present microsphere preparation is not specified. For example, anticancer agents, antibiotics, biologically active polypeptides, antipyretics, analgesics, immune stimulator, immune suppressive agents, antiinflammatory agents, antitussives, antiepileptics, antihistamic agents, hypotensive diuretics, antidiabetics, muscle relaxant, anti-ulcer agents, antidepressant, antiallergic agents, cardiotonics, antiarrhythmic agents, vasodilators, anticoagulants, hemostatics, antitubercular agents, narcotic antagonists, hormones, and the like, may be used as the pharmaceutically active ingredient.

The biodegradable polymers, which are used as a polymeric matrix for the microsphere preparation of the present invention, may be any polymer which does not show any biological activities and are easily decomposed and disappears in the living body. Such biodegradable polymers include, for example, a homopolymer of lactic acid, glycolic acid, malic acid or hydroxybutyric acid, or a copolymer of at least two of lactic acid, glycolic acid, malic acid and hydroxybutyric acid. More particularly, polylactic acid and copoly(lactic/glycolic) acid (i.e. copolymer of lactic acid and glycolic acid) which have a molecular weight of 1,000 to 500,000 are more preferable.

The content of a pharmaceutically active ingredient is not specified, and varies depending on the types of the medicaments to be used, the desired pharmacological effects, and the releasing time to be required, but it is preferably in the range of about 0.01—about 40% w/w, more preferably in the range of 0.01 to 20% w/w to the biodegradable polymers.

The microsphere preparation of the present invention is prepared by (1) dissolving two or more biodegradable polymers individually in the same or different water-immiscible organic solvent, (2) dissolving or dispersing a pharmaceutically active ingredient in one of these polymer solutions, (3) combining these solutions or dispersions to give an oil in oil (O/O) emulsion, and (4) dispersing said O/O emulsion into water to give an oil in oil in water (O/O/W) emulsion, and (5) removing the organic solvents from the oil phase of the resultant emulsion.

The O/O emulsion is easily prepared by a conventional method, for example, by dispersing or dissolving a pharmaceutically active ingredient into a solution of one of the biodegradable polymers in an organic solvent, emulsifying the dispersion or solution in other polymer(s) dissolved in the organic solvent.

The combination of these polymers may be any combination wherein each polymer can dissolve in the organic solvent but the resultant solutions are immiscible with each other, and one of these polymers (the first polymer) exists in alloy-state in other polymers (the second polymer). Such combination includes, for example, a combination of polylactic acid and copoly(lactic/glycolic) acid. The first or second polymer may be in the form of a mixture of two or more biodegradable polymers.

The water-immiscible organic solvent may be any one which can form an oil phase of O/O/W emulsion, and is volatile and has low solubility in water and can be good solvent for polymers. Such solvent includes, for example, chloroform, methylene chloride, carbon tetrachloride, and the like. Particularly, when polylactic acid and copoly(lactic/glycolic) acid are used as biodegradable polymers, methylene chloride is more preferable.

In the present invention, a polymer which is used in a larger amount than others forms a continuous phase in O/O emulsion, which polymer is designated the second polymer, and another polymer which is used in less amount than others is dispersed in said continuous phase in O/O emulsion to give microdroplets, which polymer is designated the first polymer, and hence, the polymers can be selected taking into consideration the above.

For example, when polylactic acid and copoly(lactic/glycolic) acid are used in the ratio of 2 to 4:1 by weight, and the molecular weights of both polymers are same, copoly(lactic/glycolic) acid produces microdroplets and make the first polymer. In addition, when the ratio thereof is reverse, polylactic acid produces microdroplets to make the first polymer.

In addition, the medicament in the microsphere preparation of the present invention is incorporated selectively in one of polymer solutions depending on the differences of the affinity thereof for these polymers. Thus, the microsphere preparation of the present invention can show excellent sustained release property of the medicament by having the medicament incorporated into the polymer microdroplets.

For example, when the medicament is incorporated into a continuous phase in O/O emulsion (i.e. the second polymer), it is possible to make the medicament incorporated into microdroplets of the other polymer by changing the amount of the polymers, and hence, the combination of medicament and polymers can be easily selected in the present invention.

Moreover, the particle size of the microregions in the microsphere preparation can be easily controlled. For example, since the coalescence of the particles is reduced by increasing the viscosity of the continuous phase, the O/O emulsion becomes more stable and give microspheres having microregions of smaller particle size, or when a polymer of high molecular weight is used as one of biodegradable polymers, there is obtained a microsphere preparation having microregions of small particle size.

In the present invention, the effects of the first polymer and the second polymer are as follows.

The first polymer shows higher affinity for a medicament than the second polymer so that the medicament is selectively incorporated into the first polymer.

The second polymer shows two effects. Firstly, when emulsifying the O/O emulsion into water to give the O/O/W emulsion, the second polymer keeps the medicament contained in the first polymer from dissolving out into the external aqueous solution, by which the incorporation efficiency of said ingredient is increased. Further, when the microsphere preparation of the present invention contacts with body fluid, the second polymer keeps the internal alloys of the first polymer from contacting directly with water, by which the initial burst dissolution of the medicament is prevented.

The O/O/W emulsion is prepared by emulsifying the O/O emulsion into water, and to the aqueous solution used in this step may be preferably added an emulsifying agent in order to prevent coalescence of the oil phases or coagulation of microspheres thus prepared. The emulsifying agent may be any conventional one, for example, polyhydric alcohols (e.g. polyvinyl alcohol, polyethylene glycol, etc.), surfactants, polysaccharides (e.g. chitosan, etc.), gelatin, gum arabic, and the like. The emulsifying agent is used in an amount of 0.01 to 10% w/v, preferably 0.1 to 2% w/v in an aqueous solution. It is possible to control the particle size or distribution pattern of particles in the present microsphere preparation by changing the types or amount of the emulsifying agent to be added.

The emulsification procedure is carried out by a conventional method, for example, by using stirrer with propeller, turbine impeller emulsifier, ultrasonic dispersion mixer, high-pressure emulsifier, and the like.

The subsequent removal of the organic solvents from the oil phase of the emulsion thus obtained can be conducted by the solvent evaporation method.

The solvent evaporation can be carried out by a conventional method, for example, by stirring the emulsion under heating or in vacuo. In the heat-method, the emulsion is heated with stirring by using a stirrer with propeller or turbine impeller emulsifier to remove the solvents. The stirring rate varies depending on the apparatus to be used or the amount of the emulsion, but the emulsion is stirred at about 10 to about 25,000 rpm, more preferably at 50 to 10,000 rpm. The temperature is raised taking about 0.5 to 4 hours, and the initial temperature is in the range of 0° C. to 25° C., and the highest temperature after heating is preferably in the range of 25° C. to 50° C. In the vacuo-method, the emulsion is gradually evaporated in a vacuum apparatus such as a rotary evaporator at about 0.1 to 50 mm/Hg to remove the solvents.

The microspheres obtained by the solvent evaporation method can be collected by centrifugation, filtration, etc., and washed with distilled water, and the solvents therein is removed by drying in air or in vacuo, etc., to give the microsphere preparation of the present invention. The obtained microsphere preparation is further converted in the form of a pharmaceutical preparation, if necessary, by suspending the microsphere preparation into a suitable solvent, followed by lyophilization.

The average particle size of the microsphere preparation of the present invention is in the range of about 0.01 µto 500 µm. In general, the particle size thereof is minimized by increasing the amount of the organic solvents in oil phase.

The microsphere preparation of the present invention thus obtained shows high incorporation efficiency of medicament, and as shown in Examples, the release profile of the medicament therefrom is often zero-order release type. Moreover, the release profile of the medicament from the microsphere preparation of the present invention is controlled by changing the types of combination of the first polymer and the second polymer, or changing the ratio thereof.

The microsphere preparation of the present invention can be administered as an injectable or implantable preparation to the living body, or can be used as a starting material for preparation of other pharmaceutical preparations. Suitable examples of such pharmaceutical preparations are injection preparations, preparations for oral administration, preparations for percutaneous administration, suppositories, preparations for nasal administration, preparations for buccal administration, preparations for intraocular administration, and the like.

EXAMPLES

The present invention is illustrated in more detail by the following Examples and Reference Examples, but should not be construed to be limited thereto.

Example 1

To copoly(lactic/glycolic) acid (PLGA 5020, the molar ratio of lactic acid and glycolic acid; 50:50, molecular weight; 20,000) (300 mg) and cisplatin (CDDP; average particle size: ca. 20 µm) (100 mg) is added methylene chloride (500 mg) to give Suspension A. Separately, polylactic acid (PLA 0020, molecular weight; 20,000) (600 mg) is dissolved in methylene chloride (1 g) to give Solution B. Suspension A is added to Solution B, and the mixture is emulsified with Polytron (manufactured by Kinematica Ag. Littau, Switzerland) at 12,000 rpm for 30 seconds to give an O/O emulsion having PLGA 5020 and CDDP as an internal phase.

The O/O emulsion thus obtained is added to a 0.5% aqueous polyvinyl alcohol solution (400 ml) at 15° C. by using a Pasteur pipette, and the mixture is emulsified with Polytron at 12,000 rpm for 5 minutes to give an O/O/W emulsion.

The O/O/W emulsion thus obtained is heated to 15° C. to 30° C. over a period of 3 hours during which the emulsion is stirred at 400 rpm with a paddle having 4 blades, in order to remove the solvent to give microspheres. The microspheres are collected by centrifugation, washed three times with distilled water, collected by filtration with a membrane filter, and dried under reduced pressure at room temperature for one day. The resulting microspheres have an average particle size of about 50 µm, and most of them are yellow spherical particles having a particle size of below 100 µm (Preparation 1).

Example 2

To PLGA 5020 (300 mg), CDDP (100 mg) and PLA 0020 (600 mg) is added methylene chloride (1.5 g). The mixture is emulsified with Polytron at 12,000 rpm for 30 seconds to give an O/O emulsion having CDDP distributed in the internal polymer phase. The same procedures as Example 1 are repeated to give microspheres (Preparation 2).

Example 3

To PLGA 5020 (300 mg) and CDDP (100 mg) is added methylene chloride (500 mg) to give Suspension A. Separately, polylactic acid (PLA 0010, molecular weight; 10,000) (600 mg) is dissolved in methylene chloride (1 g) to give Solution B. Suspension A is added to Solution B, and the mixture is emulsified with Polytron at 12,000 rpm for 30 seconds to give an O/O emulsion having PLGA and CDDP as an internal phase. Thereafter, the same procedures as Example 1 are repeated to give microspheres (Preparation 3).

Reference Examples 1–3

The following Reference Preparations are obtained as a reference preparation for Preparations 1 to 3.

To PLGA 5020 (900 mg) and CDDP (100 mg) is added methylene chloride (1.5 g), and the mixture is emulsified with Polytron at 12,000 rpm for 30 seconds. Thereafter, the same procedures as Example 1 are repeated to give microspheres (Reference Preparation 1).

To PLA 0020 (900 mg) and CDDP (100 mg) is added methylene chloride (1.5 g), and the mixture is emulsified with Polytron at 12,000 rpm for 30 seconds. Thereafter, the same procedures as Example 1 are repeated to give microspheres (Reference Preparation 2).

To PLA 0010 (900 mg) and CDDP (100 mg) is added methylene chloride (1 g), and the mixture is emulsified with Polytron at 12,000 rpm for 30 seconds. Thereafter, the same procedures as Example 1 are repeated to give microspheres (Reference Preparation 3).

Experiment 1

Figure 1:
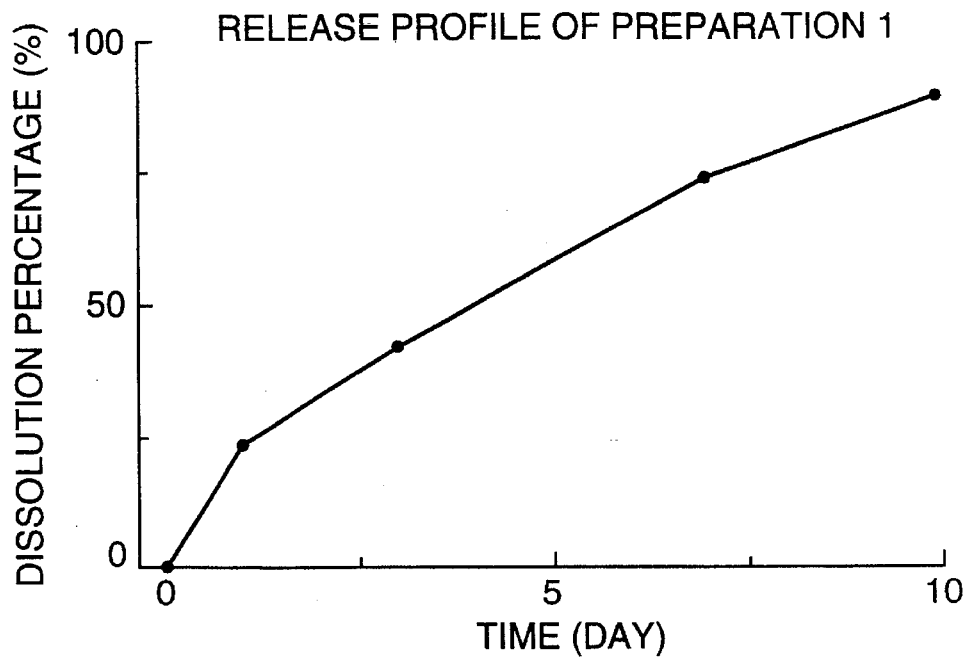
FIG. 1 shows the release profile of the active ingredient from the microsphere preparation (Preparation 1) prepared in Example 1.
Figure 2:
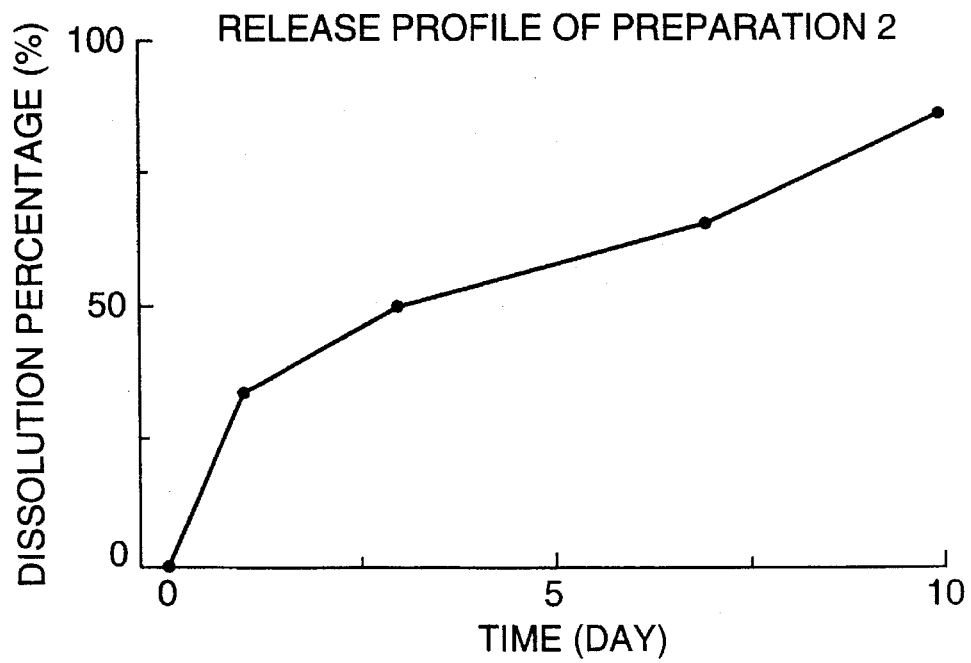
FIG. 2 shows the release profile of the active ingredient from the microsphere preparation (Preparation 2) prepared in Example 2.

The measurement of the incorporation efficiency of the medicament (percentage of the medicament being incorporated into microspheres to the medicament being used), and the dissolution test in vitro at 37° C. in an isotonic phosphate buffer (pH 7.4) were carried out in Preparations and Reference Preparations obtained above. The determination of CDDP was carried out with atomic-absorption spectrometer (HITACHI 180-80). The incorporation efficiencies of CDDP into Preparations 1–3 and Reference Preparations 1–3 are shown in Table 1. The incorporation efficiencies of CDDP into microspheres prepared according to the present invention (Preparations 1–3) were significantly higher than those of Reference Preparations. The dissolution test results of Preparations 1 and 2 are shown in FIG. 1 and FIG. 2. As is clear from these results, the microspheres prepared by the present invention show higher incorporation efficiency of the pharmaceutically active ingredient than the microspheres prepared by using one polymer, and the release profiles of CDDP from Preparations 1 and 2 are zero-order release type.

TABLE 1

Incorporation Efficiency of CDDP into Microspheres

| Preparation | Incorporation Efficiency (%) |
| --- | --- |
| Preparation 1 | 83.5% |
| Preparation 2 | 93.3% |
| Preparation 3 | 89.4% |
| Reference Preparation 1 | 73.7% |
| Reference Preparation 2 | 62.3% |
| Reference Preparation 3 | 50.2% |

Example 4

A solution of PLA 0020 (333 mg) in acetonitrile (1 ml) and a solution of human calcitonin (1 mg) in methanol (0.5 ml) are combined, and the mixture is evaporated under reduced pressure to remove the solvent. To the resultant is added methylene chloride (500 mg) to give Solution A. Separately, PLGA 5020 (667 mg) is dissolved in methylene chloride (1 g) to give Solution B. Solution A is added to Solution B, and the mixture is emulsified with Polytron at 12,000 rpm for 30 seconds. Thereafter, the same procedures as Example 1 are repeated to give microspheres (Preparation 4).

Experiment 2

The incorporation efficiency of human calcitonin of Preparation 4 obtained in Example 4 was measured by high performance liquid chromatography. The results are shown in Table 2, which indicates that the human calcitonin was incorporated by nearly 100% (i.e. 95.3%) into microspheres of Preparation 4.

TABLE 2

Incorporation Efficiency of human calcitonin

| | Incorporation Efficiency (%) |
| --- | --- |
| Preparation 4 | 95.3% |

Example 5

To PLA 0010 (300 mg) and (4S)-3-[(2S)-N-[(1S)-1-ethoxycarbonyl-3-phenylpropyl]alanyl]-1-methyl-2-oxo-4-imidazolidinecarboxylic acid hydrochloride (100 mg) is added methylene chloride (500 mg) to give Solution A. Separately, PLGA 5020 (600 mg) is dissolved in methylene chloride (1 g) to give Solution B. Solution A is added to Solution B, and the mixture is emulsified with Polytron at 12,000 rpm for 30 seconds. Thereafter, the same procedures as Example 1 are repeated to give microspheres (Preparation 5).

Reference Example 4

To PLGA 5020 (900 mg) and (4S)-3-[(2S)-N-[(1S)-1-ethoxycarbonyl-3-phenylpropyl]alanyl]-1-methyl-2-oxo-4-imidazolidinecarboxylic acid hydrochloride (100 mg) is added methylene chloride (1 g), and the mixture is emulsified with Polytron at 12,000 rpm for 30 seconds. Thereafter, the same procedures as Example 1 are repeated to give microspheres (Reference Preparation 4), which is a reference for Preparation 5.

Experiment 3

The incorporation efficiencies of (4S)-3-[(2S)-N-[(1S)-1-ethoxycarbonyl-3-phenylpropyl]alanyl]-1-methyl-2-oxo-4-imidazolidinecarboxylic acid hydrochloride into the microspheres prepared in Example 5 and Reference Example 4 were measured with absorption spectrophotometer (HITACHI 2000, W1=280 nm, W2=220 nm). In Preparation 5, 12.4 mg of (4S)-3-[(2S)-N-[(1S)-1-ethoxy -carbonyl-3-phenylpropyl]alanyl]-1-methyl-2-oxo-4-imidazolidine carboxylic acid hydrochloride was incorporated into 1 g of the microspheres. On the contrary, (4S)-3-[(2S)-N-[(1S)-1-ethoxy -carbonyl-3-phenylpropyl]alanyl]-1-methyl-2-oxo-4-imidazolidine -carboxylic acid hydrochloride was hardly incorporated into the microspheres in Reference Preparation 4.

Example 6

PLGA 5020 (300 mg) and TRH (100 mg) are mixed, and thereto is added methylene chloride (500 mg) to give Solution A. Separately, PLA 0020 (600 mg) is dissolved in methylene chloride (1 g) to give Solution B. Solution A is added to Solution B, and the mixture is emulsified with Polytron at 12,000 rpm for 30 seconds. Thereafter, the same procedures as Example 1 are repeated to give microspheres.

Example 7

PLGA 5020 (300 mg) and LHRH (100 mg) are mixed, and thereto is added methylene chloride (500 mg) to give Solution A. Separately, PLA 0020 (600 mg) is dissolved in methylene chloride (1 g) to give Solution B. Solution A is added to Solution B, and the mixture is emulsified with Polytron at 12,000 rpm for 30 seconds. Thereafter, the same procedures as Example 1 are repeated to give microspheres.

Example 8

PLGA 5020 (300 mg) and Vitamin B12 (100 mg) are mixed, and thereto is added methylene chloride (500 mg) to give Solution A. Separately, PLA 0020 (600 mg) is dissolved in methylene chloride (1 g) to give Solution B. Solution A is added to Solution B, and the mixture is emulsified with Polytron at 12,000 rpm for 30 seconds. Thereafter, the same procedures as Example 1 are repeated to give microspheres.

Example 9

Figure 4:
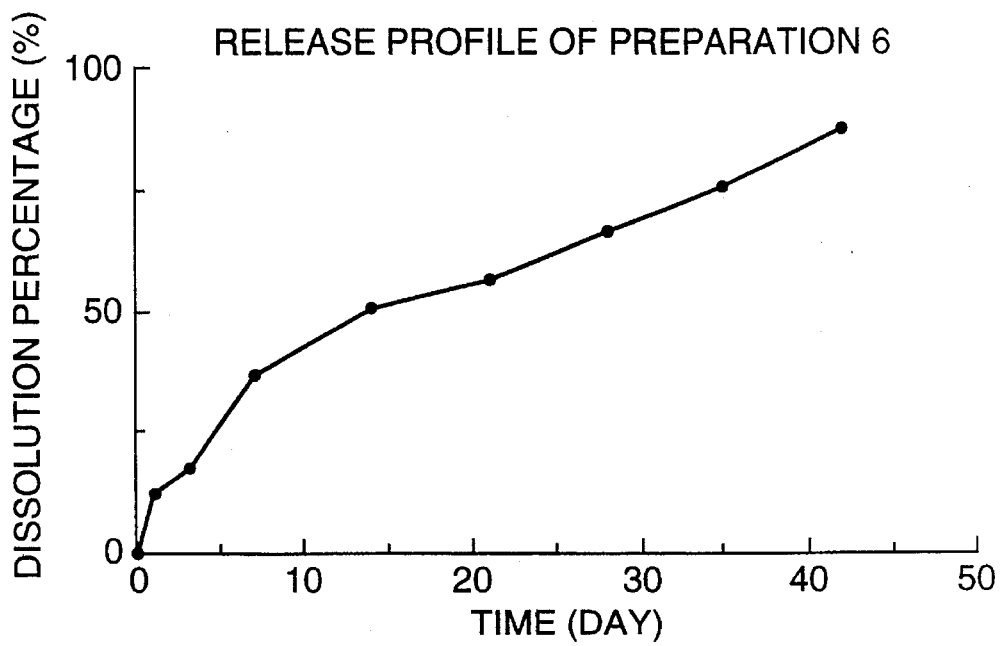
FIG. 4 shows the release profile of the active ingredient from the microsphere preparation (Preparation 6) prepared in Example 9.

To PLGA 5020 (90 mg) and CDDP (average particle size: 1 µm) (50 mg) is added methylene chloride (150 mg) to give Suspension A. Separately, PLA 0020 (360 mg) is dissolved in methylene chloride (600 mg) to give Solution B. Suspension A is added to Solution B, and the mixture is emulsified with Polytron at 12,000 rpm for 30 seconds to give an O/O emulsion having PLGA and CDDP as an internal phase. Thereafter, the same procedures as Example 1 are repeated to give microspheres (Preparation 6). The dissolution test result of the Preparation 6 is shown in FIG. 4.

Example 10

Figure 5:
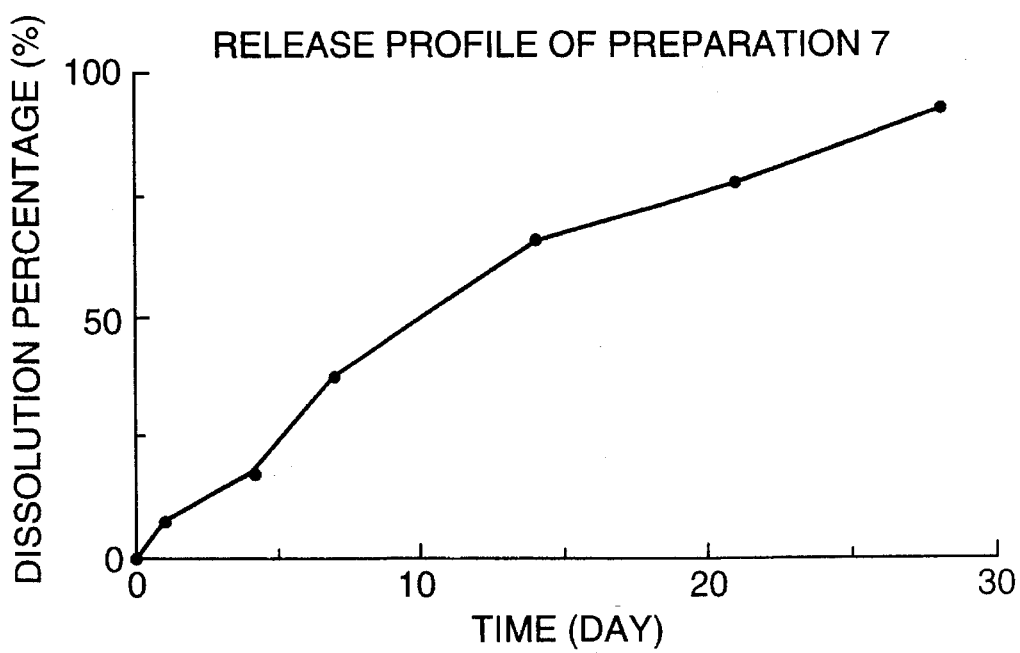
FIG. 5 shows the release profile of the active ingredient from the microsphere preparation (Preparation 7) prepared in Example 10.

To PLGA 5020 (90 mg) and CDDP (average particle size: 1 µm) (50 mg) is added methylene chloride (150 mg) to give Suspension A. Separately, PLA 0020 (270 mg) and polylactic acid having the molecular weight of 130,000 (90 mg) are dissolved in methylene chloride (825 mg) to give Solution B. Suspension A is added to Solution B, and the mixture is emulsified with Polytron at 2,000 rpm for 30 seconds to give an O/O emulsion having PLGA and CDDP as an internal phase. Thereafter, the same procedures as Example 1 are repeated to give microspheres (Preparation 7). The dissolution test result of the Preparation 7 is shown in FIG. 5.

Effects of the Invention

According to the present invention, there is obtained a microsphere preparation which shows high incorporation efficiency of pharmaceutically active ingredient, and can release said ingredient for a long period, which is prepared by preparing an O/O emulsion using two or more kinds of biodegradable polymers, dispersing said O/O emulsion into water to give an O/O/W emulsion, followed by evaporating the solvent from said O/O/W emulsion.

What is claimed is:

1. A sustained release multi-core microsphere preparation, which comprises
   (1) microregions comprising a first biodegradable polymer,
   (2) a continuous region comprising a second biodegradable polymer, in which the microregions are distributed, and
   (3) a therapeutically effective amount of at least one pharmaceutically active ingredient selectively retained in the microregions of said first biodegradable polymer;
   said microsphere preparation being obtained by
      (i) preparing an oil-in-oil emulsion comprising water immiscible organic solvent, the first biodegradable polymer, the second biodegradable polymer and the pharmaceutically active ingredient having higher affinity for the first biodegradable polymer than for the second biodegradable polymer, the biodegradable polymers being selected from the group consisting of polylactic acid and a copolymer of lactic acid and glycolic acid, and the oil-in-oil emulsion having microdroplets of the first biodegradable polymer dispersed in a continuous oil phase of the second biodegradable polymer,
      (ii) dispersing the oil-in-oil emulsion in an aqueous solution to give an oil-in-oil-in-water emulsion, and
      (iii) removing the water-immiscible organic solvent from the oil phases of the resulting oil-in-oil-in-water emulsion.

2. The microsphere preparation according to claim 1, wherein said first biodegradable polymer is a copolymer of lactic acid and glycolic acid and said second biodegradable polymer is polylactic acid.

3. The microsphere preparation according to claim 1, wherein said first biodegradable polymer is polylactic acid and said second biodegradable polymer is a copolymer of lactic acid and glycolic acid.

4. The microsphere preparation according to claim 2, wherein said pharmaceutically active ingredient in a member selected from the group consisting of cisplatin, TRH, LHRH, and vitamin $B_{12}$.

5. The microsphere preparation according to claim 3, wherein said pharmaceutically active ingredient is a member selected from the group consisting of calcitonin and (4S)-3-{(2S)-N-{(1S)-1-ethoxycarbonyl-3-phenylpropyl}alanyl}-1-methyl-2-oxo-4-imidazolidinecarboxylic acid hydrochloride.

6. The microsphere preparation according to any one of claims 2, 3, 1, 4, or 5 wherein said microsphere preparation has an average particle size in the range of 0.01 µm to 500 µm.

7. A sustained release multi-core microsphere preparation having an average particle size in the range of 0.01 µm to 500 µm, which comprises
   (1) microregions comprising a copolymer of lactic acid and glycolic acid,
   (2) a continuous region comprising polylactic acid, in which the microregions are distributed, and
   (3) a therapeutically effective amount of cisplatin selectively retained in said microregions comprising a copolymer of lactic acid and glycolic acid.

8. A method of producing a multi-core microsphere preparation which comprises the steps of:
   (1) preparing an oil-in-oil emulsion comprising a water immiscible organic solvent, a first biodegradable polymer, a second biodegradable polymer and at least one pharmaceutically active ingredient having higher affinity for the first biodegradable polymer than for the second biodegradable polymer, said biodegradable polymers being selected from the group consisting of polylactic acid and a copolymer of lactic acid and glycolic acid,
   (2) dispersing said oil-in-oil emulsion in an aqueous solution to give an oil-in-oil-in-water emulsion, and (3) removing said water-immiscible organic solvent from the oil phases of the resulting oil-in-oil-in-water emulsion to obtain a multi-core microsphere comprising microregions distributed in a continuous region and a pharmaceutically active ingredient retained selectively in the microregions or in the continuous region.

9. A method according to claim 8, wherein the first polymer and the second polymer are used in a ratio of 1:2 to 4 by weight.

10. The microsphere preparation according to claim 1, wherein the polylactic acid and the copolymer of lactic acid and glycolic acid are those having a molecular weight of 1,000 to 500,000.

11. The microsphere preparation according to claim 1, wherein the first polymer is a mixture of two or more biodegradable polymers.

12. The microsphere preparation according to claim 1, wherein the second polymer is a mixture of two or more biodegradable polymers.

13. The microsphere preparation according to any one of claims 2, 3, 1, 4, 5, wherein the first polymer and the second polymer are used in a ratio of 1:2 to 4 by weight.

14. The microsphere preparation according to any one of claims 2, 3, 1, 4, 5, wherein a content of the pharmaceutically active ingredient is in a range of 0.01 to 40%.

* * * * *